United States Patent [19]

Bellus et al.

[11] Patent Number: 4,622,395

[45] Date of Patent: Nov. 11, 1986

[54] PHENOXAZINE AND PHENOTHIAZINE DYES AND LEUCO FORMS THEREOF

[75] Inventors: Peter A. Bellus, Minneapolis; Roger A. Mader, Stillwater, both of Minn.

[73] Assignee: Minnesota Mining and Manufacturing Company, St. Paul, Minn.

[21] Appl. No.: 656,460

[22] Filed: Oct. 1, 1984

[51] Int. Cl.[4] .................. C07D 265/38; C07D 279/18; C07D 279/24; C07D 279/30
[52] U.S. Cl. ...................................... 544/37; 544/103
[58] Field of Search ................................ 544/37, 103

[56] References Cited

U.S. PATENT DOCUMENTS

| | | | |
|---|---|---|---|
| 2,646,367 | 6/1951 | Davis et al. | 117/36 |
| 3,447,944 | 6/1969 | Werner et al. | 117/36.2 |
| 3,681,347 | 8/1972 | Herz et al. | 544/103 X |
| 3,828,035 | 8/1974 | Baumann et al. | 544/103 X |
| 3,928,339 | 12/1975 | Mundlos et al. | 544/103 |
| 4,009,162 | 2/1977 | Mundlos et al. | 544/103 |
| 4,018,763 | 4/1977 | Moser et al. | 544/103 |
| 4,309,255 | 1/1982 | Gendler et al. | 204/2 |
| 4,423,226 | 12/1983 | Mohr et al. | 544/103 X |
| 4,561,001 | 12/1985 | Gunn et al. | 346/218 |

FOREIGN PATENT DOCUMENTS 48-52778 7/1973 Japan .

OTHER PUBLICATIONS

"Pharmacological Chemistry Journal", vol. 10, p. 83 (1976), by G. A. Khutormenko et al.

Primary Examiner—Richard L. Raymond
Attorney, Agent, or Firm—Donald M. Sell; James A. Smith; Lorraine R. Sherman

[57] ABSTRACT

Novel phenoxazine and phenothiazine dyes have the formula

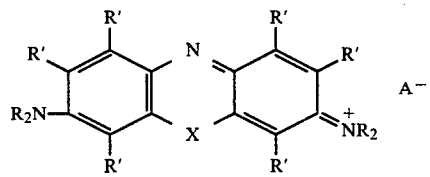

wherein
X can be —S— or —O—;
each R can be the same or different and is independently selected from
(1) hydrogen,
(2) an unsubstituted aryl or alkyl group or these groups substituted by up to four groups selected from alkyl, alkoxy, cyano, hydroxy, halogen, nitro, mercapto, alkylsulfonyl, arylsulfonyl, and Z, where Z is as defined below, wherein all alkyl and alkoxy groups have 1 to 20 carbon atoms; and
(3) Z, wherein Z can be

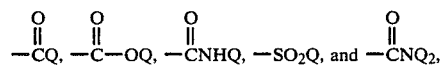

wherein each Q can be the same or different and is independently selected from
(1) hydrogen,
(2) an unsubstituted aryl or alkyl group or these groups substituted by up to four groups selected from alkyl, alkoxy, cyano, hydroxy, halogen, nitro, mercapto, alkylsulfonyl, arylsulfonyl, and Z, where Z is as defined above, wherein all alkyl and alkoxy groups have 1 to 20 carbon atoms; and
R' is the same or different and is independently selected from hydrogen, halogen, alkyl or alkoxy of 1 to 6 carbon atoms or these groups substituted by up to 3 halogen atoms; and
A is an anion;
with the proviso that R and L can have up to a total of 5 carbonyl and sulfonyl groups, and with the proviso that the average value of a Taft Constant and of a Hammett Constant for the two R groups on at least one 3- or 7-position nitrogen atom is greater than 1.0 for a Taft Constant and greater than +0.1 for a Hammett Constant.

23 Claims, No Drawings

PHENOXAZINE AND PHENOTHIAZINE DYES AND LEUCO FORMS THEREOF

FIELD OF THE INVENTION

The present invention relates to novel oxazine and thiazine dyes useful in all dyeing applications such as those involving fabrics, plastics, and paper. In another aspect, leuco phenoxazine and phenothiazine dyes are disclosed which are useful, for example, in imaging systems as well as in carbonless paper.

BACKGROUND ART

Certain classes of phenothiazine and phenoxazine dyes are known and have been used for a variety of purposes for many years. Examples of these phenothiazine dyes include Methylene Blue (C.I. 52015), Thiocarmine R (C.I. 52035), Lauth's Violet (C.I. 5200), and Azure B (C.I. 52010). These dyes range from turquoise (Methylene Blue Dmax=660 nm) to violet (Lauth's Violet Dmax=590 nm) in color. Similarly, phenoxazines include Capri Blue (C.I. 51000), Brilliant Cresyl Blue (C.I. 51010), and Nile Blue (C.I. 51180), which also range in color from turquoise to blue.

The leuco forms of these classes of phenoxazine and phenothiazine dyes are useful in imaging systems. Copikem II ™ (Hilton-Davis) is a benzoyl leuco thiazine and Pergascript Turquoise S2G ™ (Ciba-Geigy is a benzoyl leuco oxazine. Both give rise to turquoise color on reversion to the dye form and as such are useful in carbonless systems (e.g., see U.S. Pat. No. 2,646,367), thermographic systems (e.g., see U.S. Pat. 3,447,944), and electrochromic systems (e.g., see U.S. Pat. No. 4,309,255). Their use is limited to applications where blue is the only color necessary. Two- or three-color imaging is not possible due to the limited range of colors known in the thiazine and oxazine dye classes.

Compounds of the formula

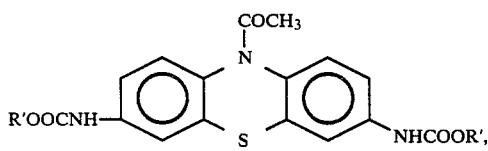

wherein R' is methyl, ethyl, or iso-butyl, are disclosed by G. A. Khutormenko et al. in "Pharmacological Chemistry Journal", Vol. 10, at page 83 (1976), having utility as a pharmacologically active compound having antiarrhythmic properties. These compounds have not been used as dyes or color formers.

Japanese Kokai No. 73 52 778 (and abstract) discloses phenoxazine leuco dyes capable of providing dyes in shades of blue.

SUMMARY OF THE INVENTION

Briefly, this invention provides certain classes of novel leuco oxazine and thiazine dyes having at least one electron withdrawing substituent on the amine groups at the 3- and 7-positions.

These dyes can be used to prepare dyes, i.e., the oxidized form of leuco dyes, capable of providing red, yellow, magenta, and orange colors that have good stability to heat and light. The prior art did not recognize that phenoxazine or phenothiazine dyes in the color range of purple to yellow, i.e., having a λmax less than about 600 nm, preferably less than 580 nm, could be prepared. It has been believed in the art that all phenoxazine and phenothiazine dyes have blue to turquoise colors.

In the present application:

the phenoxazine and phenothiazine ring system is numbered as follows:

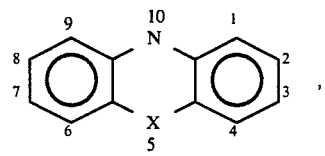

wherein X can be —O— or —S—,

"leuco dye" means a colorless or lightly colored dye which can be oxidized to a colored form;

"aryl" means phenyl or napthyl;

"arylene" means phenylene or naphthylene;

"lower alkyl" means alkyl containing 1 to 4 carbon atoms;

"lower alkoxy" means alkoxy containing 1 to 4 carbon atoms;

"aliphatic" means a straight-chain or branched-chain hydrocarbon; and

"halogen" means fluorine, chlorine, bromine, and iodine.

The phenoxazine and phenothiazine dyes and leuco dyes of the invention are useful in photothermographic color constructions as disclosed in Assignee's copending patent application, U.S. Ser. No. 656,690, filed the same date as this application.

DETAILED DESCRIPTION

Phenoxazine and phenothiazine dyes of the present invented can be represented by the formula:

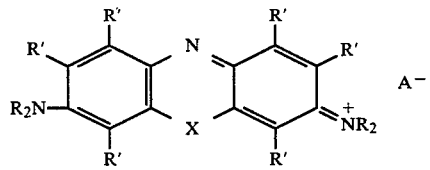

wherein

X can be —S— or —O—;

each R can be the same or different and is independently selected from (1) hydrogen, (2) an unsubstituted aryl or alkyl group or these groups substituted by up to four groups selected from alkyl, alkoxy, cyano, hydroxy, halogen, nitro, mercapto, alkylsulfonyl, arylsulfonyl, and Z, wherein Z is as defined below, wherein all alkyl and alkoxy groups have 1 to 20 carbon atoms, and preferably are lower alkyl and alkoxy, and (3) Z, wherein Z can be

wherein each Q can be the same or different and is independently selected from (1) hydrogen, (2) an unsubstituted aryl or alkyl group or these groups substituted by up to four groups selected from alkyl, alkoxy, cyano, hydroxy, halogen, nitro, mercapto, alkylsulfonyl, arylsulfonyl, and Z, where Z is as defined above, wherein all alkyl and alkoxy groups have 1 to 20 carbon atoms, and preferably are lower alkyl and alkoxy; and R' is the same or different and can be independently selected from hydrogen, halogen (fluorine, chlorine, bromine, iodine), alkyl or alkoxy of 1 to 6 carbon atoms or these groups substituted by up to 3 halogen atoms; and A is an anion;

with the proviso that R can have up to a total of 5 carbonyl and sulfonyl groups, preferably up to 3 carbonyl and sulfonyl groups, and with the proviso that the average of the Taft Constant and the Hammett Constant for the two R groups on at least one, and preferably both, 3- and 7-position nitrogen atom is greater than 1.0, preferably greater than 1.5 for the Taft Constant, and greater than +0.1, preferably +0.15 for the Hammett Constant as defined by a Hammett or Taft Constant given in Lange's Handbook of Chemistry, 12th ed., McGraw-Hill, NY, pp. 3-134 to 3-137 (1979).

The dyes of the invention can have molecular weights of up to 2,000, preferably up to 700.

Groups more electron withdrawing than hydrogen include but are not limited to those specified in (3) above. Preferable electron withdrawing groups include trifluoroethyl, acetyl, benzoyl, cyanoethyl, trifluoroacetyl, and methanesulfonyl. Not included are methyl, ethyl, or hydrogen.

Examples of A$^-$ include NO$_3^-$, Cl$^-$, Br$^-$, I$^-$, benzoate, acetate, tetrafluoroborate, tetraphenylborate, and p-toluenesulfonate, although any water- or organic solvent-solubilizing anion can be useful.

Representative examples of dyes of the invention include

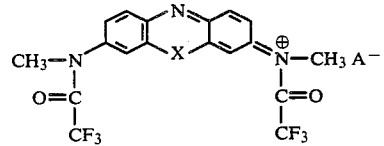

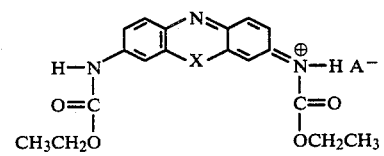

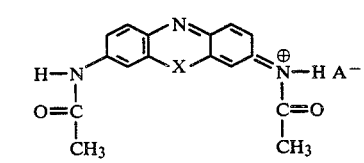

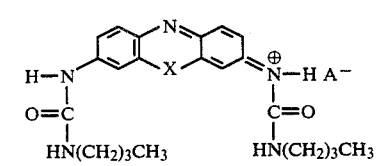

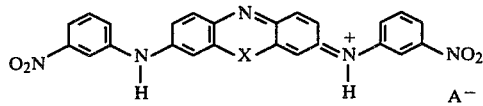

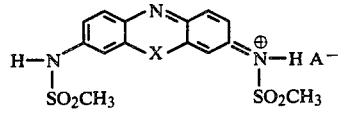

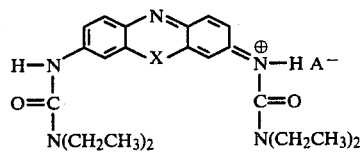

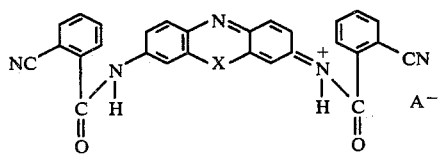

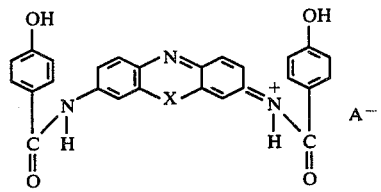

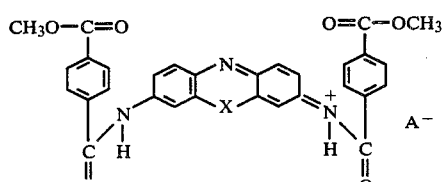

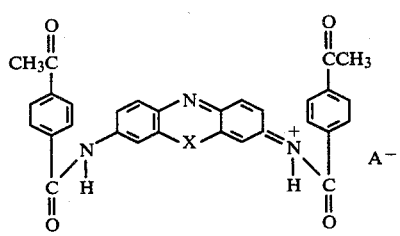

wherein X can be —O— or —S—, and

A$^-$ can be NO$_3^-$, Cl$^-$, Br$^-$, I$^-$, benzoate, acetate, tetrafluoroborate, tetraphenylborate, and p-toluenesulfonate, although any water- or organic solvent-solubilizing anion can be useful.

Preferred dyes include:

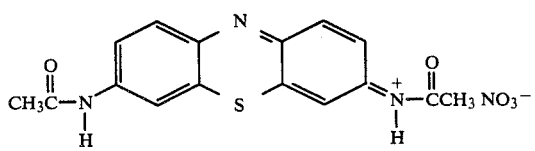

-continued

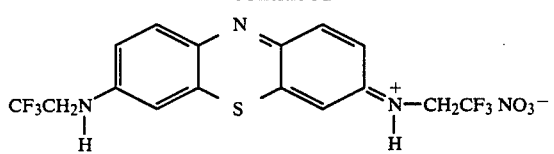
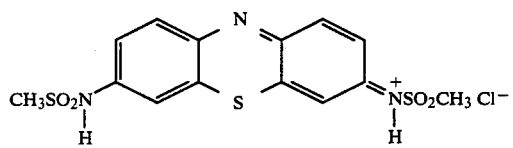
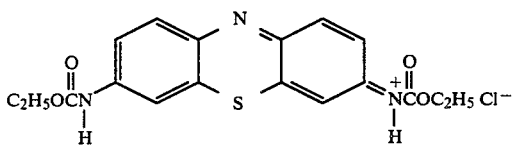
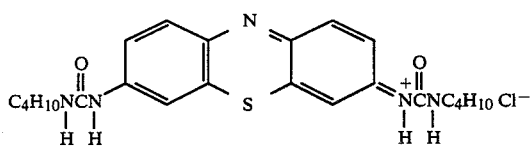
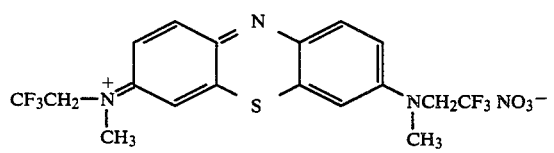
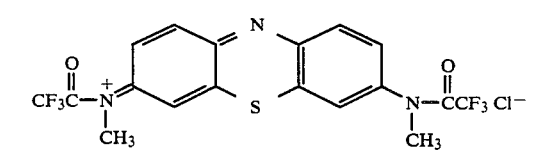
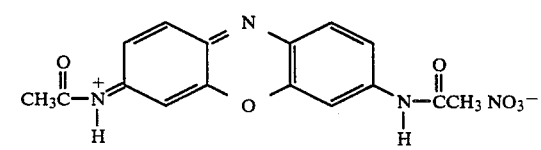
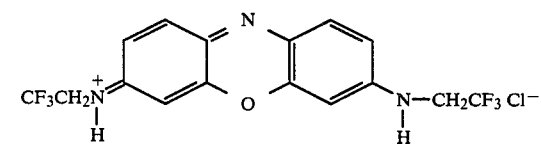
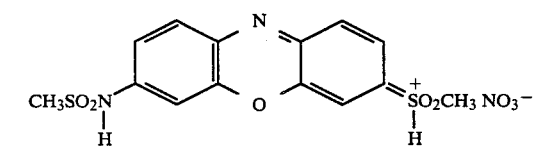
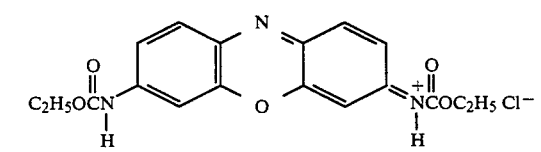

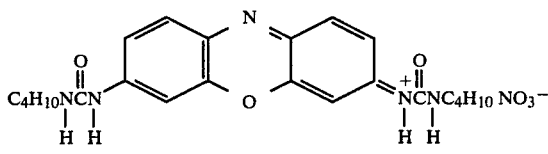
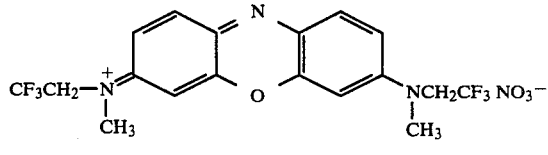
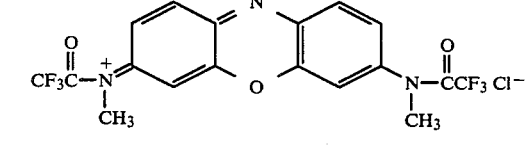
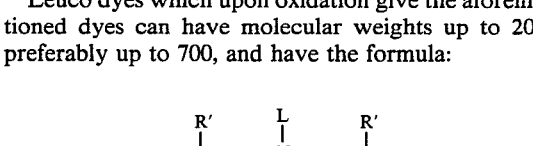
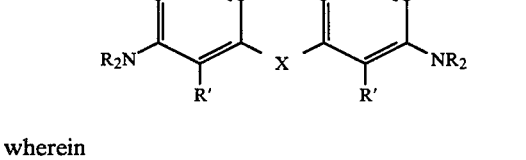

Leuco dyes which upon oxidation give the aforementioned dyes can have molecular weights up to 2000, preferably up to 700, and have the formula:

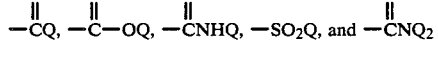

wherein
X is —S— or —O—;
each R can be the same or different and is independently selected from
(1) hydrogen,
(2) an unsubstituted aryl or alkyl group or these groups substituted by up to four groups selected from alkyl, alkoxy, cyano, hydroxy, halogen, nitro, mercapto, alkylsulfonyl, arylsulfonyl, and Z, where Z is as defined below, wherein all alkyl and alkoxy groups have 1 to 20 carbon atoms and preferably are lower alkyl and alkoxy; and
(3) Z, wherein Z can be $$-\overset{O}{\underset{\|}{C}}Q, \ -\overset{O}{\underset{\|}{C}}-OQ, \ -\overset{O}{\underset{\|}{C}}NHQ, \ -SO_2Q, \ and \ -\overset{O}{\underset{\|}{C}}NQ_2$$

wherein each Q can be the same or different and is independently selected from
(1) hydrogen,
(2) an unsubstituted aryl or alkyl group or these groups substituted by up to four groups selected from alkyl, alkoxy, cyano, hydroxy, halogen, nitro, mercapto, alkylsulfonyl, arylsulfonyl, and Z, where Z is as defined below, wherein all alkyl and alkoxy groups have 1 to 20 carbon atoms and preferably are lower alkyl and alkoxy, and
R' is the same or different and can be independently selected from hydrogen, halogen (fluorine, chlorine, bromine, iodine), alkyl or alkoxy of 1 to 6 carbon atoms or these groups substituted by up to 3 halogen atoms; and
L is Z or hydrogen;

with the proviso that R and L can have up to a total of 5 carbonyl and sulfonyl groups, preferably up to 3 carbonyl and sulfonyl groups, and with the proviso that when X=—S— and

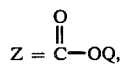

then L is only

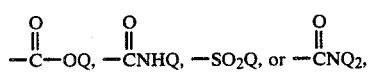

wherein each Q can be the same or different and can be independently selected from
(1) hydrogen,
(2) an unsubstituted aryl or alkyl group or these groups substituted by up to four groups selected from alkyl, alkoxy, cyano, hydroxy, halogen, nitro, mercapto, alkysulfonyl, arylsulfonyl, and Z, where Z is as defined above, wherein all alkyl and alkoxy groups have 1 to 20 carbon atoms and preferably are lower alkyl and alkoxy; or

wherein Q' can be selected from
(1) hydrogen,
(2) an unsubstituted aryl or alkyl group or these groups substituted by up to four groups selected from alkyl, alkoxy, cyano, hydroxy, halogen, nitro, mercapto, alkylsulfonyl, arylsulfonyl, and Z, where Z is as defined above, wherein all alkyl and alkoxy groups have 1 to 20 carbon atoms and preferably are lower alkyl and alkoxy,
with the proviso that the average value of a Taft Constant and of a Hammett Constant for the two R groups on at least one 3- or 7-position nitrogen atom is greater than 1.0 for a Taft Constant and greater than +0.1 for a Hammett Constant.

The leuco dyes and dyes of the invention can be prepared as is known in the art by acylation of an unsubstituted phenoxazine or phenothiazine compound (step I of Flow Chart I below) to provide an N-acylated phenoxazine or phenothiazine compound. Nitration, in acetic acid (step II of Flow Chart I below), as is known in the art provides, after recrystallization, the 3,7-dinitro phenoxazine or phenothiazine compound. Hydrogenation catalyzed by platinum metal (step III of Flow Chart I below) gives the corresponding diamino compounds. Treatment of the diamino compound with the appropriate alkylating or acylating reagent at room temperature in the presence of a base such as pyridine, triethylamine, or sodium hydroxide, (step IV of Flow Chart I below) gives the diamino substituted leuco dye. The leuco dye product of step IV can be converted to its oxidized colored dye form by oxidation in alcoholic silver nitrate at room temperature.

The preparation of the leuco dye can be accomplished in four steps, and the dye in five steps, as shown in the following flow charts, wherein R, Z, X, L, Q, and A⁻ are as defined above and Y can be halogen. Two methods of preparation are shown, these being the preferred methods.

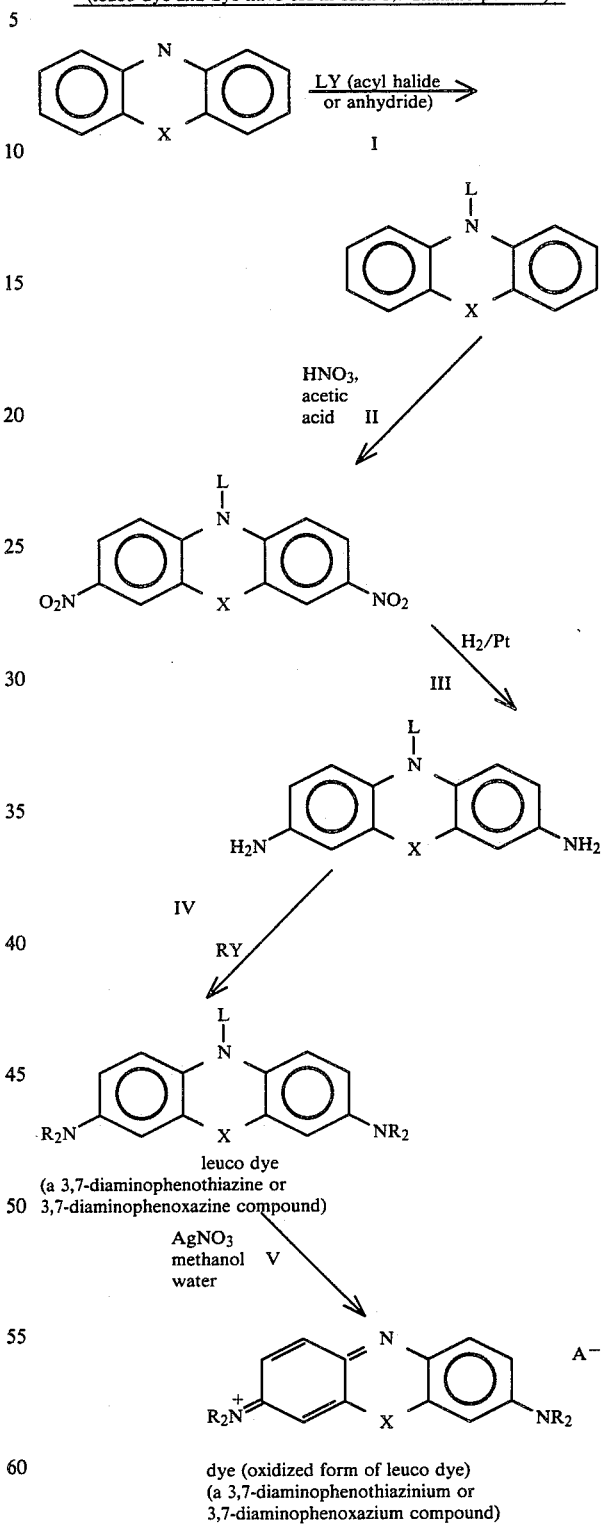

Alternatively, the preparation can begin with a known phenoxazine or phenothazine dye having at least one hydrogen atom in at least one 3 and 7 diamino position. The dye can be reduced with dithionite (step I of Flow Chart II, below) and extracted into methylene chloride. This solution is treated with an alkylating or acylating reagent at room temperature in the presence of a base such as pyridine, triethylamine or sodium hydroxide (step II of Flow Chart II below). The resulting compound is a leuco dye and can be oxidized to the dye form using alcoholic silver nitrate at room temperature (step V of Flow Chart II). Alternatively, the hydrogen leuco dye can be prepared by treatment with mineral acid (step III of Flow Chart II). This hydrogen leuco dye can be treated with a different alkylating or acylating agent (step IV of Flow Chart II) to give a different leuco dye. Oxidation (step VI) can give the dye form.

The choice of method (Flow Chart I or II) depends on the particular substituents in the desired dye or leuco dye molecule.

carbonless paper. The dyes of the invention are useful in all dyeing application, for example, with fabrics, plastics, and paper.

Objects and advantages of this invention are further illustrated by the following examples, but the particular materials and amounts thereof recited in these examples, as well as other conditions and details, should not be construed to unduly limit this invention.

EXAMPLE 1

Leuco Dye Preparation

To 5.26 g of thionin in 100 ml of methylene chloride were added four grams of sodium dithionite and one gram of sodium hydroxide in 10 ml of water. The mixture was stirred for hour. To this was then added 10 ml of phenylchloroformate (over a 20 minute period) and

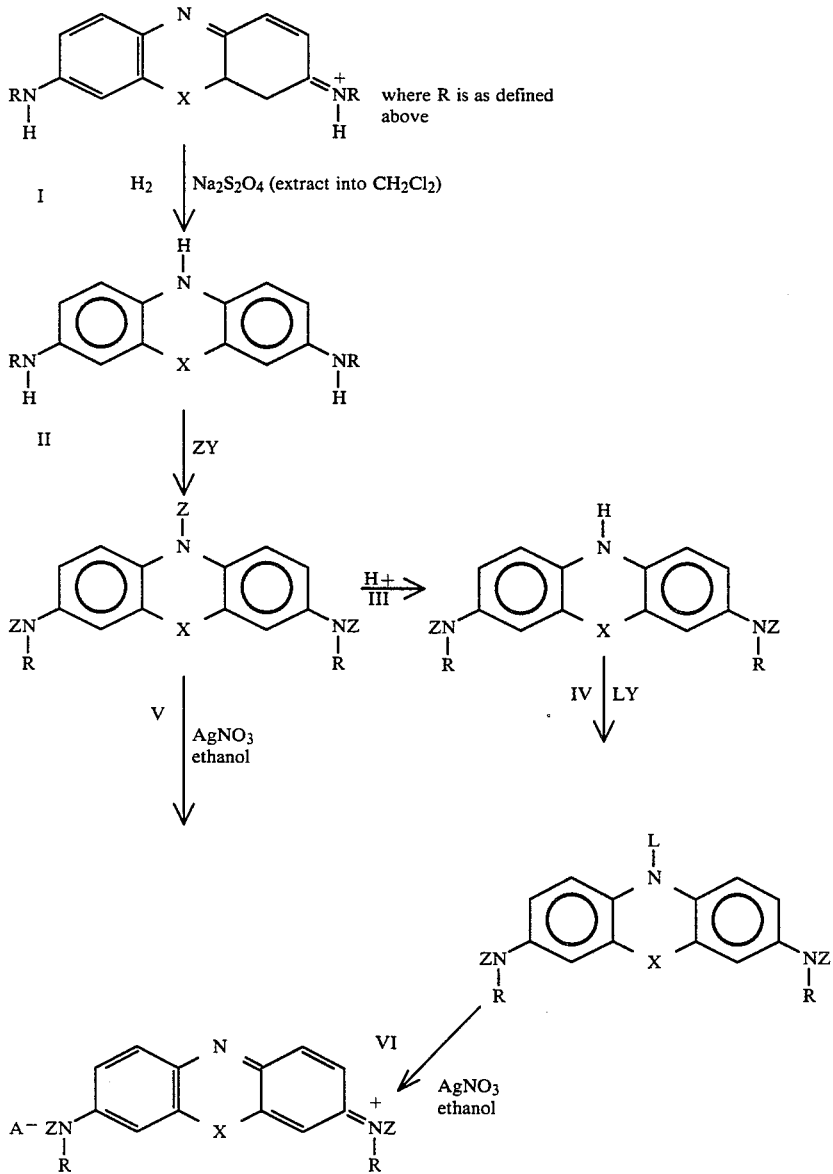

The leuco dyes of the invention are useful in imaging systems, such as photothermographic and thermographic processes that rely on dye oxidation, and also in 10 ml of 50% sodium hydroxide. After stirring an additional 30 minutes 50 ml of water was added and the slurry filtered. A portion of the solid was chromatographed on silica gel eluted with 70:30 methylene chloride:ethyacetate to give 3,7-diphenylcarbamoyl(10H)-phenothiazine which was identified by spectroscopic analysis.

EXAMPLE 2

Leuco Dye Preparation

A mixture containing 6.54 g of N-acetyl-3,7-dinitrophenoxazine and 2.0 of ten percent platinum on carbon in 200 ml of 1:1 ethanol:tetrahydrofuran was hydrogenated at 1.4 kg/cm$^2$ (20 psi) for three hours. The catalyst was filtered and the solvent removed to give 4.8 gm. This was taken up in 70 ml of pyridine and treated with 3.0 g of ethyl chloroformate. The mixture was added to dilute HCl and the product extracted into ethyl acetate. The ethyl acetate layer was washed, dried, and the solvent removed to give 2.6 g of crude N-actyl-3,7-diethylcarbamoylphenoxazine.

A solution containing 1.4 g of the just-mentioned phenoxazine compound in 10 ml of methanol and 8 ml of acetone was treated with 10 ml of concentrated hydrochloric acid and heated to reflux for 30 minutes. The mixture was cooled to 0° C. and the solids filtered. The solid was slurried in 10 percent sodium carbonate. To this was then added 50 ml of 1:1 acetone:ethylacetate. The mixture was filtered and the layers split. The organic phase was dried over sodium sulfate and the solvent removed to give crude 3,7-diethylcarbamoyl(10H)phenoxazine.

Phosgene was added to a suspension of 3,7-diethylcarbamoyl(10H)phenoxazine compound in 20 ml of methylene chloride. After 30 minutes most of the solid dissolved and most of the phosgene was removed with heat and a stream of nitrogen. The residue was taken up in 20 ml of methylene chloride and treated with excess N-butylamine. The mixture was stirred 30 minutes then poured into dilute HCl. The slurry was filtered and the organic phase separated. The residue from the organic phase and the solid were combined and chromatographed over silica gel eluted with ethyl acetate. The solid was recrystallized from ethyl acetate-acetone to give 0.25 g of the corresponding n-butylurea having the formula

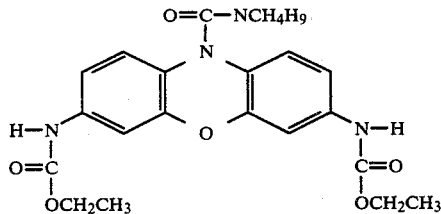

which was identified by spectroscopic analysis.

EXAMPLE 3

Leuco Dye Preparation

A solution of 2.55 g on N-acetyl-3,7-diaminophenoxazine in 15 ml of pyridine and 10 ml of methylene chloride was stirred at room temperature and to it was added over a 10 minute period 2.5 g of methanesulfonyl chloride. The mixture was stirred for one hour then poured into excess 5% hydrochloric acid. The mixture was extracted several times with ethyl acetate. The solid obtained from the extracts was recrystalized from ethyl acetate to give 2.4 g of N-acetyl-3,7-di(methylsulfonamido)(10H)phenoxazine, which was identified by spectroscopic analysis.

EXAMPLE 4

Leuco dye preparation

A mixture containing 1 g of N-acetyl-3,7-diamino (10H) phenoxazine, 3 g of the triflate ester of trifluoroethanol (60.9% in benzene), 0.8 g of triethylamine in 20 ml of benzene was heated to reflux for 24 hours. The mixture was poured into dilute HCl and the product extracted into ethyl acetate. The extract was chromatographed on silica gel to give N-acetyl-3,7-di-(1,1,1-trifluoroethylamino)(10H)phenoxazine, which was identified by spectroscopic analysis.

EXAMPLE 5

Leuco Dye Preparation

To a suspension of 0.2 g of the product of Example 3 in 17 ml of water was added 0.3 g of sodium hydroxide. The blue solution was heated to 60° C. for 30 minutes. After cooling to room temperature hydrochloric acid was added until the mixture was acidic. The product was extracted into ethyl acetate then chromatographed on silica gel to give 0.05 g of 3,7-di(methysulfonamido)(10H)phenoxazine, which was identified by spectroscopic analysis.

EXAMPLE 6

Preparation of Oxazine Dye and Use 0.1 g of the leuco dye of Example 4 was dissolved in 5 ml of a saturated solution of silver nitrate in ethanol. The solution was allowed to stand for several hours as the color gradually darkened. A strip of bond paper was dipped into the solution and was dyed a purple-magenta color.

EXAMPLE 7

Preparation of Thiazine Dye and Use 0.1 g of 10-acetyl-3,7-bis(acetamido)phenothiazine was dissolved in 5 ml of a saturated solution of silver nitrate in ethanol. The solution was allowed to stand for several hours as the color gradually darkened. A strip of bond paper was dipped into the solution and was dyed a purple color.

EXAMPLE 8

Use of Leuco Dye in Photothermographic System

Leuco dyes (see Table I below) were added to the following formulation and evaluated for Dmin, Dmax, development time, and image color, in a 'dry silver' photothermographic system.

'Dry silver' formulation 14.1 silver behenate homogenized in toluene at 12% solids
71.1 g toluene
6.1 g ethanol
8.3 g Butvar B-76 ™ (polyvinyl butyral resin, Monsanto Corp.)
1.0 ml solution of 4.3 g ZnCl$_2$ in 100 ml ethanol
The above was mixed well and coated at 76 micrometers thick wet on heavyweight paper and dried at 85° C. (185° F.) for 4 minutes.

50 g ethanol
42.5 g acetone
7.5 g Butvar B-76
0.1 g Cyasorb UV 5411 TM (UV absorber, American Cyanamid)
0.5 g phthalic acid The above was mixed well. 0.05 g leuco dye was added to 8 g of the above and was coated at 76 micrometers thick (3 mil) wet on the above silver-containing material and air dried.

The sample was exposed through a step wedge to 40,000 lux for 20 seconds and developed at 160° C. for the time specified in Table 1. Dmin and Dmax were measured on a Macbeth RD514 densitometer using a visual filter.

The imaging characteristics are shown in TABLE I for the leuco dyes of samples 1 to 11 which have the structures indicated.

TABLE I

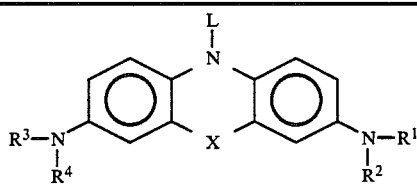

| Sample | $R^1, R^3$ | $R^2, R^4$ | L | X | $D_{min}$ | $D_{max}$ | Development time | Image color |
|---|---|---|---|---|---|---|---|---|
| 1 | H | $C(O)CH_3$ | $C(O)CH_3$ | S | 0.16 | 0.22 | 30 sec. | pink |
| 2 | H | $C(O)OCH_3$ | H | S | 0.49 | 1.70 | 30 sec. | purple |
| 3 | H | $C(O)OC_2H_5$ | $C(O)NHC_4H_9$ | O | 0.57 | 1.08 | 5 sec. | magenta |
| 4 | H | $C(O)CF_3$ | H | O | 1.50 | 1.78 | 2 sec. | purple |
| 5 | H | $C(O)CF_3$ | $C(O)NHC_4H_9$ | O | 0.31 | 1.07 | 30 sec. | purple |
| 6 | H | $SO_2CH_3$ | H | O | 1.84 | 2.09 | 3 sec. | orange |
| 7 | H | $C(O)CCl_3$ | $C(O)NHC_4H_9$ | O | 0.29 | 0.51 | 15 sec. | magenta |
| 8 | H | $C(O)CHCl_2$ | $C(O)NHC_4H_9$ | O | 0.40 | 0.48 | 12 sec. | red |
| 9 | H | $C(O)CH_2Cl$ | $C(O)NHC_4H_9$ | O | 0.34 | 1.20 | 20 sec. | red/orange |
| 10 | H | $CH_2CF_3$ | $C(O)CH_3$ | O | 0.18 | 0.57 | 4 min. | blue ($\lambda$max 595) |
| 11 | $CH_3$ | $C(O)CF_3$ | $C(O)NHC_4H_9$ | O | 0.35 | 0.64 | 25 sec. | brown |

All of the leuco dyes gave useful colored images.

Various modofications and alterations of this invention will become apparent to those skilled in the art without departing from the scope and spirit of this invention, and it should be understood that this invention is not to be unduly limited to the illustrative embodiments set forth herein.

We claim:

1. A phenoxazine or phenothiazine dye represented by the formula:

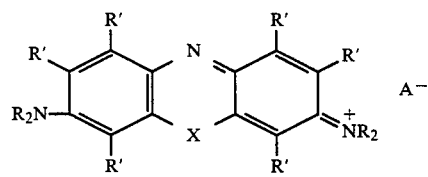

wherein
X is —S— or —O—;
each R is the same or different and is independently selected from
(1) hydrogen,
(2) an unsubstituted aryl or alkyl group or these groups substituted by up to four groups selected from alkyl, alkoxy, cyano, hydroxy, halogen, nitro, mercapto, and Z, where Z is as defined below, wherein all alkyl and alkoxy groups have 1 to 20 carbon atoms, and
(3) Z, wherein Z is

wherein Q is independently selected from
(1) hydrogen,
(2) an unsubstituted aryl or alkyl group or these groups substituted by up to four groups selected from alkyl, alkoxy, cyano, hydroxy, halogen, nitro, mercapto, and Z, where Z is as defined above, wherein all alkyl and alkoxy groups have 1 to 20 carbon atoms; and
R' is the same or different and is independently selected from (1) hydrogen or halogen, and (2) alkyl or alkoxy of 1 to 6 carbon atoms or these groups substituted by up to 3 halogen atoms; and
A is an anion;
with the proviso that when X=—O—, R cannot be halomethyl or cyanomethyl, and with the proviso that R can have up to a total of 5 carbonyl and sulfonyl groups, and with the proviso that the average value of a Taft Constant and of a Hammett Constant for the two R groups on at least one 3- or 7-position nitrogen atom is greater than 1.5 for a Taft constant and greater than +0.15 for a Hammett Constant; and with the proviso that said dye has a $\lambda$max of less than 580 nm.

2. A leuco phenoxazine or phenothiazine dye represented by the formula

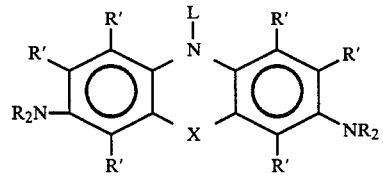

wherein
X is —S— or —O—;
each R is the same or different and is independently selected from (1) hydrogen,
(2) an unsubstituted aryl or alkyl group or these groups substituted by up to four groups selected from alkyl, alkoxy, cyano, hydroxy, halogen, nitro, mecapto, and Z, where Z is as defined below, wherein all aklyl and alkoxy groups have 1 to 20 carbon atoms; and
(3) Z, wherein Z is

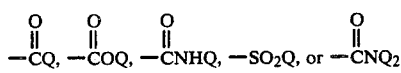

wherein Q is independently selected from
(1) hydrogen,
(2) an unsubstituted aryl or alkyl group or these groups substituted by up to four groups selected from alkyl, alkoxy, cyano, hydroxy, halogen, nitro, mercapto, and Z, where Z is as defined above, wherein all alkyl and alkoxy groups have 1 to 20 carbon atoms; and
R' is the same or different and is independently selected from (1) hydrogen or halogen, and (2) alkyl or alkoxy of 1 to 6 carbon atoms or these groups substituted by up to 3 halogen atoms; and
L is Z;

with the proviso that R and L can have up to a total of 5 carbonyl and sulfonyl groups, and with the proviso that when X=S— and

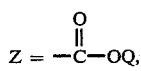

then L is only

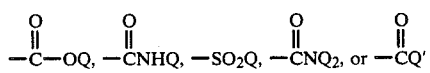

wherein each Q can be the same or different and is independently
(1) hydrogen,
(2) an unsubstituted aryl or alkyl group or these groups substituted by up to four groups selected from alkyl, alkoxy, cyano, hydroxy, halogen, nitro, mercapto, and Z, where Z is as defined above in the definition of R, wherein all alkyl and alkoxy groups have 1 to 20 carbon atoms; and wherein Q' is selected from
(1) hydrogen,
(2) an unsubstituted aryl group or this group substituted by up to four groups selected from alkyl, alkoxy, cyano, hydroxy, halogen, nitro, mercapto, and Z wherein Z is as defined in the definition of R above, wherein all alkyl and alkoxy groups have 1 to 20 carbon atoms, with the proviso that if only one R is

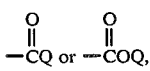

then L cannot also be the same

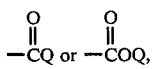

with the proviso that when X is —O—, Z cannot be

and with the proviso that the average value of a Taft Constant and of a Hammett Constant for the two R groups on at least one 3- or 7-position nitrogen atom is greater than 1.5 for a Taft Constant and greater than +0.15 for a Hammett Constant, and with the proviso that said leuco dye can be oxidized to a dye having a λmax of less than 580 nm.

3. The phenothiazine dye according to claim 1 having the formula

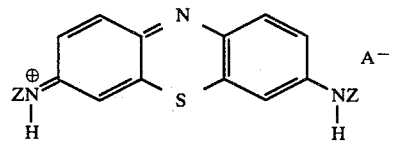

wherein Z is as defined in claim 1.

4. The phenoxazine dye according to claim 1 having the formula

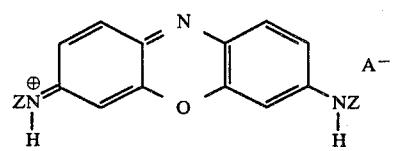

wherein Z is as defined in claim 1.

5. The leuco phenothiazine dye according to claim 2 having the formula

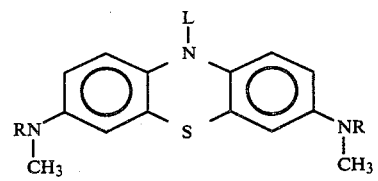

wherein R is as previously defined.

6. The leuco phenoxazine dye according to claim 1 having the formula

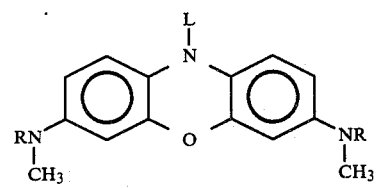

wherein R is as previously defined.

7. The leuco dye according to claim 2 wherein Z is

and wherein each Q is independently selected from H, lower alkyl of $C_1$ to $C_4$, or phenyl.

8. The leuco dye according to claim 2 wherein L is

wherein Q is H, lower alkyl of $C_1$ to $C_4$, or phenyl.

9. A phenoxazine or phenothiazine dye represented by the formula:

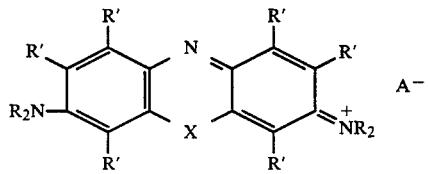

wherein
X is —S— or —O—;
each R is the same or different and is independently selected from
(1) hydrogen,
(2) an unsubstituted aryl or alkyl group or these groups substituted by up to four groups selected from alkyl, alkoxy, cyano, hydroxy, halogen, nitro, mercapto, and Z, where Z is as defined below, wherein all alkyl and alkoxy groups have 1 to 20 carbon atoms, and
(3) Z, wherein Z is

wherein Q is independently selected from
(1) hydrogen,
(2) an unsubstituted aryl or alkyl group or these groups substituted by up to four groups selected from alkyl, alkoxy, cyano, hydroxy, halogen, nitro, mercapto, wherein all alkyl and alkoxy groups have 1 to 20 carbon atoms; and
R' is the same or different and is independently selected from (1) hydrogen or halogen, and (2) alkyl or alkoxy of 1 to 6 carbon atoms or these groups substituted by up to 3 halogen atoms; and
A is an anion;
with the proviso that
(1) at least one R group is Z, or
(2) at least one R group on each nitrogen atom attached to the 3- and 7-ring position carbon atoms is trifluoroethyl.

10. The phenoxazine or phenothiazine dye according to claim 9 wherein at least one R group is Z.

11. A phenoxazine or phenothiazine dye represented by the formula:

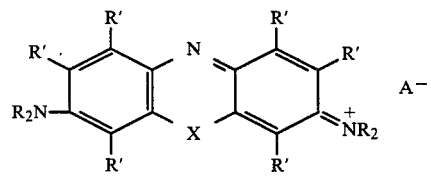

wherein
X is —S— or —O—;
each R is the same or different and is independently selected from
(1) hydrogen, (2) an unsubstituted aryl or alkyl group or these groups substituted by up to four groups selected from alkyl, alkoxy, cyano, hydroxy, halogen, nitro, mercapto, and Z, where Z is as defined below, wherein all alkyl and alkoxy groups have 1 to 20 carbon atoms, and
(3) Z, wherein Z is

wherein Q is independently selected from
(1) hydrogen,
(2) an unsubstituted aryl or alkyl group or these groups substituted by up to four groups selected from alkyl, alkoxy, cyano, hydroxy, halogen, nitro, mercapto, wherein all alkyl and alkoxy groups have 1 to 20 carbon atoms; and
R' is the same or different and is independently selected from (1) hydrogen or halogen, and (2) alkyl or alkoxy of 1 to 6 carbon atoms or these groups substituted by up to 3 halogen atoms; and
A is an anion;
with the proviso that at least one R group on each nitrogen atom attached in the 3- and 7-ring carbon positions is Z or trifluoroethyl.

12. The phenoxazine or phenothiazine dye according to claim 9 wherein at least one R group is

[structures shown]

13. A leuco phenoxazine or phenothiazine dye represented by the formula

[structure shown]

wherein
X is —S— or —O—;

each R is the same or different and is independently selected from
(1) hydrogen,
(2) an unsubstituted aryl or alkyl group or these groups substituted by up to four groups selected from alkyl, alkoxy, cyano, hydroxy, halogen, nitrogen, mercapto, and Z, where Z is as defined below, wherein all alkyl and alkoxy groups have 1 to 20 carbon atoms, and
(3) Z, wherein Z is

wherein Q is independently selected from
(1) hydrogen,
(2) an unsubstituted aryl or alkyl group or these groups substituted by up to four groups selected from alkyl, alkoxy, cyano, hydroxy, halogen, nitro, and mercapto, wherein all alkyl and alkoxy groups have 1 to 20 carbon atoms; and R' is the same or different and is independently selected from hydrogen, halogen, alkyl or alkoxy of 1 to 6 carbon atoms or these groups substituted by up to 3 halogen atoms; and L is Z;

with the proviso that
(1) at least one R group is Z, or
(2) at least one R group on each nitrogen atom attached to the 3- and 7-ring position carbon atoms is trifluoroethyl; and with the proviso that when X=—S— and

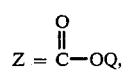

then L is only

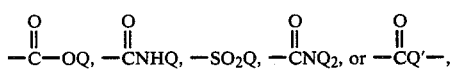

wherein each Q can be the same or different and is independently
(1) hydrogen,
(2) an unsubstituted aryl or alkyl group or these groups substituted by up to four groups selected from alkyl, alkoxy, cyano, hydroxy, halogen, nitro, and mercapto, wherein all alkyl and alkoxy groups have 1 to 20 carbon atoms;
and wherein Q' is selected from
(1) hydrogen,
(2) an unsubstituted aryl group or this group substituted by up to four groups selected from alkyl, alkoxy, cyano, hydroxy, halogen, nitro, and mercapto, wherein all alkyl and alkoxy groups have 1 to 20 carbon atoms;
with the proviso that if only one R is

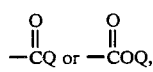

then L cannot also be the same

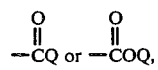

with the proviso that the average value of a Taft Constant and of a Hammett Constant for the two R groups on both the 3- and 7-position nitrogen atoms is greater than 1.5 for a Taft Constant and greater than +0.15 for a Hammett constant, and with the proviso that said leuco dye can be oxidized to a dye having a λmax of less than 580 nm.

14. A symmetric leuco phenoxazine or phenothiazine dye represented by the formula

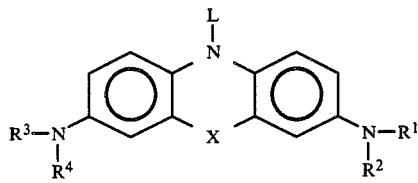

wherein
when X is —O—;
then, $R^1$ and $R^3$ both are H or $CH_3$;
$R^2$ and $R^4$ both are $C(O)CH_3$, $C(O)OCH_3$, $C(O)OC_2H_5$, $C(O)CF_3$, $SO_2CH_3$, $C(O)CCl_3$, $C(O)CHCl_2$, $C(O)CH_2Cl$, or $CH_2CF_3$, and
L is $C(O)CH_3$ or $C(O)NHC_4H_9$; and
wherein
when X is —S—,
then,
$R^1$ and $R^3$ both are H or $CH_3$;
$R^2$ and $R^4$ both are $C(O)CH_3$, $C(O)OCH_3$, $C(O)OC_2H_5$, $C(O)CF_3$, $SO_2CH_3$, $C(O)CCl_3$, $C(O)CHCl_2$, $C(O)CH_2Cl$, or $CH_2CF_3$, and
L is $C(O)NHC_4H_9$.

15. A leuco phenoxazine or phenothiazine dye represented by the formula

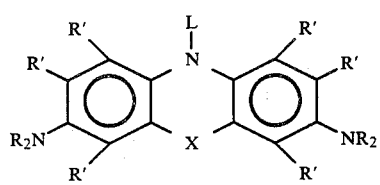

wherein
X is —S— or —O—;
each R is the same or different and is independently selected from
(1) hydrogen,
(2) an unsubstituted aryl or alkyl group or these groups substituted by up to four groups selected from alkyl, alkoxy, cyano, hydroxy, halogen, nitrogen, mercapto, and Z, where Z is as defined below, wherein all alkyl and alkoxy groups have 1 to 20 carbon atoms, and
(3) Z, wherein Z is

wherein Q is independently selected from
(1) hydrogen, (2) an unsubstituted aryl or alkyl group or these groups substituted by up to four groups selected from alkyl, alkoxy, cyano, hydroxy, halogen, nitro, mercapto, and Z, where Z is as defined above, wherein all alkyl and alkoxy groups have 1 to 20 carbon atoms; and R' is the same or different and is independently selected from (1) hydrogen or halogen, and (2) alkyl or alkoxy of 1 to 6 carbon atoms or these groups substituted by up to 3 halogen atoms; and L is Z;

with the proviso that R and L can have up to a total of 5 carbonyl and sulfonyl groups, and with the proviso that when X=—S— and

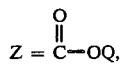

then L is only

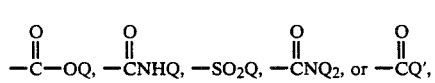

wherein each Q can be the same or different and is independently (1) hydrogen, (2) an unsubstituted aryl or alkyl group or these groups substituted by up to four groups selected from alkyl, alkoxy, cyano, hydroxy, halogen, nitro, mercapto and Z, where Z is as defined above, wherein all alkyl and alkoxy groups have 1 to 20 carbon atoms;

and wherein Q' is selected from (1) hydrogen, (2) an unsubstituted aryl group or this group substituted by up to four groups selected from alkyl, alkoxy, cyano, hydroxy, halogen, nitro, mercapto, and Z wherein Z is as defined above, wherein all alkyl and alkoxy groups have 1 to 20 carbon atoms; and with the proviso that if only one R is

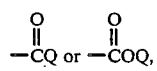

then L cannot also be the same

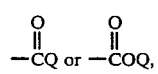

and with the proviso that the average value of a Taft Constant and of a Hammett Constant for the two R groups on both the 3- and 7-position nitrogen atoms is greater than 1.5 for a Taft constant and greater than +0.15 for a Hammett constant, and with the proviso that said leuco dye can be oxidized to a dye having a λmax of less than 580 nm.

16. The phenoxazine dye according to claim 9 having the formula

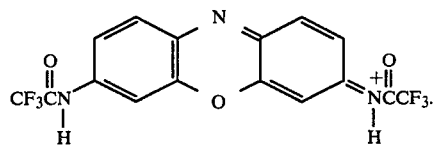

17. The phenoxazine dye according to claim 9 having the formula

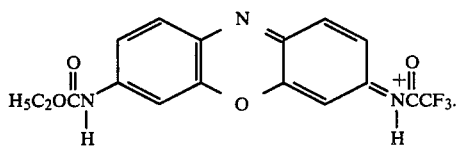

18. The phenoxazine dye according to claim 9 having the formula

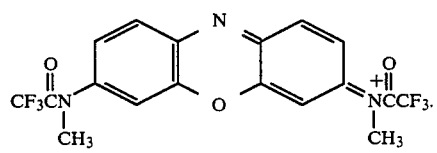

19. The phenothiazine dye according to claim 9 having the formula

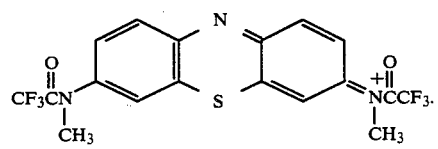

20. The leuco dye according to claim 15 having the formula

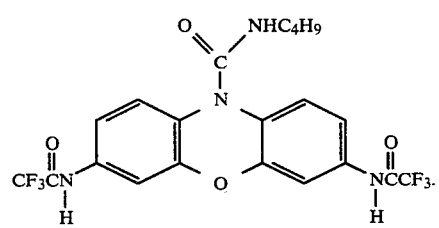

21. The leuco dye according to claim 13 having the formula

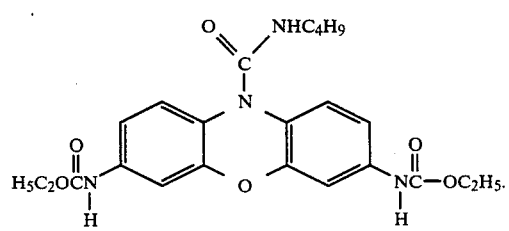

22. The leuco dye according to claim 15 having the formula

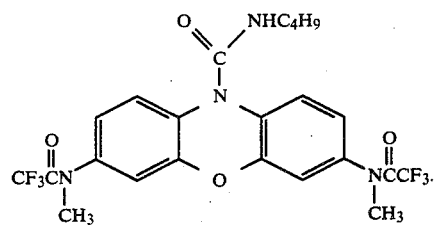
23. The leuco dye according to claim 15 having the formula
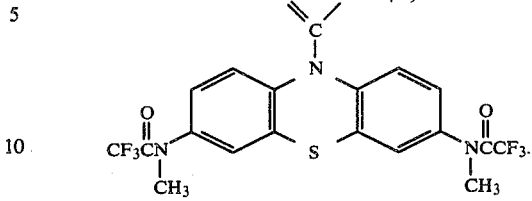
* * * * *